(12) United States Patent
Eifler et al.

(10) Patent No.: US 8,424,528 B2
(45) Date of Patent: Apr. 23, 2013

(54) VENTILATION DEVICE

(75) Inventors: Martin Eifler, Glückstadt (DE); Gerd Schulz, Schenefeld (DE)

(73) Assignee: Weinmann Geräte für Medizin GmbH & Co. KG, Hamburg (DE)

( * ) Notice: Subject to any disclaimer, the term of this patent is extended or adjusted under 35 U.S.C. 154(b) by 1384 days.

(21) Appl. No.: 12/151,892

(22) Filed: May 9, 2008

(65) Prior Publication Data

US 2008/0276943 A1    Nov. 13, 2008

Related U.S. Application Data

(63) Continuation-in-part of application No. 11/035,038, filed on Jan. 13, 2005, now abandoned.

(30) Foreign Application Priority Data

Jan. 14, 2004    (DE) .......................... 10 2004 002 125

(51) Int. Cl.
| | |
|---|---|
| A61M 16/00 | (2006.01) |
| A62B 18/02 | (2006.01) |
| A62B 18/08 | (2006.01) |
| F16L 23/00 | (2006.01) |
| F16L 21/02 | (2006.01) |
| F16L 21/00 | (2006.01) |
| B65D 63/02 | (2006.01) |
| B65D 63/06 | (2006.01) |

(52) U.S. Cl.
USPC ............ 128/206.27; 128/203.29; 128/205.25; 128/206.21; 128/206.28; 128/207.11; 128/207.13; 128/206.12; 285/367; 285/373; 285/419; 24/20 R; 24/22; 24/24

(58) Field of Classification Search ............. 128/203.29, 128/205.25, 206.21, 206.27, 206.28, 207.11, 128/207.13, 206.12; 285/367, 373, 419; 24/20 R, 22, 24

See application file for complete search history.

(56) References Cited

U.S. PATENT DOCUMENTS

| 4,693,242 A * | 9/1987 | Biard ...................... 128/204.26 |
| 6,491,034 B1 * | 12/2002 | Gunaratnam et al. ... 128/204.18 |
| 7,195,012 B2 * | 3/2007 | Lurie ....................... 128/203.11 |
| 2008/0210241 A1 * | 9/2008 | Schulz et al. ............ 128/206.21 |

* cited by examiner

*Primary Examiner* — Patricia Bianco
*Assistant Examiner* — Nihir Patel
(74) *Attorney, Agent, or Firm* — Lucas & Mercanti, LLP; Klaus P. Stoffel

(57) ABSTRACT

A device used for ventilation includes a ventilation mask that can be connected to a respiratory gas hose. The ventilation mask has a respiratory gas hose coupling that is movably connected by a joint with the base of the ventilation mask. The joint is a ball-and-socket joint, which has an inner part that is shaped like a spherical segment and an outer shell for guiding the inner part. The outer shell is constructed from at least two shell segments that can be connected with each other.

15 Claims, 9 Drawing Sheets

VENTILATION DEVICE

CROSS-REFERENCE TO RELATED APPLICATIONS

The present application is a Continuation-In-Part application of Ser. No. 11/035,038 filed Jan. 13, 2005 now abandoned.

BACKGROUND OF THE INVENTION

1. Field of the Invention

The present invention relates to a ventilation device, which is designed as a ventilation mask that can be connected to a respiratory gas hose and which has a respiratory gas hose coupling that is movably connected by a joint with a base of the ventilation mask.

2. Description of the Related Art

Ventilation masks of this type can be designed both as nasal masks and full-face masks. Typically, a movable hose connection is used, which is mounted in the area of the base of the mask in a way that allows it to rotate.

The prior-art joints for realizing the movable hose connection are still not capable of satisfactorily meeting the entire range of requirements that must be placed on these devices, especially when they are to be used by patients who are not particularly mechanically inclined. For one thing, the joints must provide a high degree of mobility in order to promote a high degree of wearing comfort by minimizing as much as possible the introduction of forces into the ventilation mask through the respiratory gas hose. In addition, it is necessary to ensure a low overall weight and a high degree of reliability for a large number of different application boundary conditions.

SUMMARY OF THE INVENTION

The objective of the present invention is to provide a device of the aforementioned type in such a way that a high degree of functionality is combined with a high degree of reliability, simple assembly, and a high degree of mechanical stability.

In accordance with the invention, this objective is achieved by constructing the joint as a ball-and-socket joint, which has an inner part that is shaped like a spherical segment and an outer shell for guiding the inner part, and by forming the outer shell from at least two shell segments that can be connected with each other.

In accordance with the invention, the stated objective can also be achieved by constructing the joint as a ball-and-socket joint, which has an inner part that is shaped like a spherical segment and an outer shell for guiding the inner part, and by forming the outer shell from at least one shell segment which, in the installed state, has elastically deformable guide elements which, in the operating state, are stabilized by a securing ring.

Designing the joint as a ball-and-socket joint provides both a high degree of rotational mobility and a high degree of mechanical stability. Dividing the outer shell into at least two shell segments that can be connected with each other provides a simple means of installing the inner part that is shaped like a spherical segment. At the same time, a sufficiently large external covering of the inner part can be provided by the outer shell, so that unintentional separation of the parts of the joint from each other is prevented. In particular, this prevents parts of the joint from being pushed into the mask when force is applied. This is very important especially for full-face masks.

To achieve a mechanically stable embodiment, it is helpful if the first shell segment is mounted on the base of the mask.

To ensure simple assembly, the inner part is formed as part of the hose coupling.

Simple handling is assisted by constructing the second shell segment as a ring.

Assembly with few manipulations can be achieved if the shell segments are coupled by at least one snap connection.

Mechanical stability can be further increased if the second shell segment is installed near a securing device.

Improved guidance of the inner part can be achieved if the second shell segment has a guide web that applies force on the inner part.

In another fastening variant, the securing device is locked with the first shell segment by a clamp.

It is also possible for the securing device to be locked with the first shell segment by a catch.

In addition, it is conceivable for the securing device to be screwed together with the first shell segment.

To achieve a high degree of rotational mobility of the joint, it is helpful to construct the outer shell at least regionally in the form of spherical segments.

A combination of a high degree of mobility and a high degree of mechanical stability can be achieved if there is line contact between the first shell segment and the inner part.

To achieve a simple geometry of the components, it is helpful if the securing device is constructed as a closed ring.

To facilitate the removal of injection-molded parts from the molds, it is proposed that the securing device be formed as a hinged ring.

In another variant, the securing device is provided with internal teeth.

Local decoupling of different functions can be achieved by arranging the joint outside of the ventilation mask between the base of the mask and the respiratory gas hose.

Good accessibility of the parts that are used can be achieved by arranging the securing device on the outside with respect to the interior of the mask.

In accordance with an embodiment that has an especially responsive design, the securing device is arranged on the inside with respect to the interior of the mask.

Low-tolerance guidance of the inner part combined with simple assembly and a high degree of mechanical stability is achieved if the securing device with its internal teeth at least regionally encloses teeth of the first shell segment.

A relatively large guide surface for the inner part can be provided by designing both shell segments to guide the inner part.

Discontinuities due to production tolerances in the area of the guide surface for the inner part can be avoided if only the first shell segment is designed for guiding the inner part, while the second shell segment is designed for mechanical stabilization of the second shell segment.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
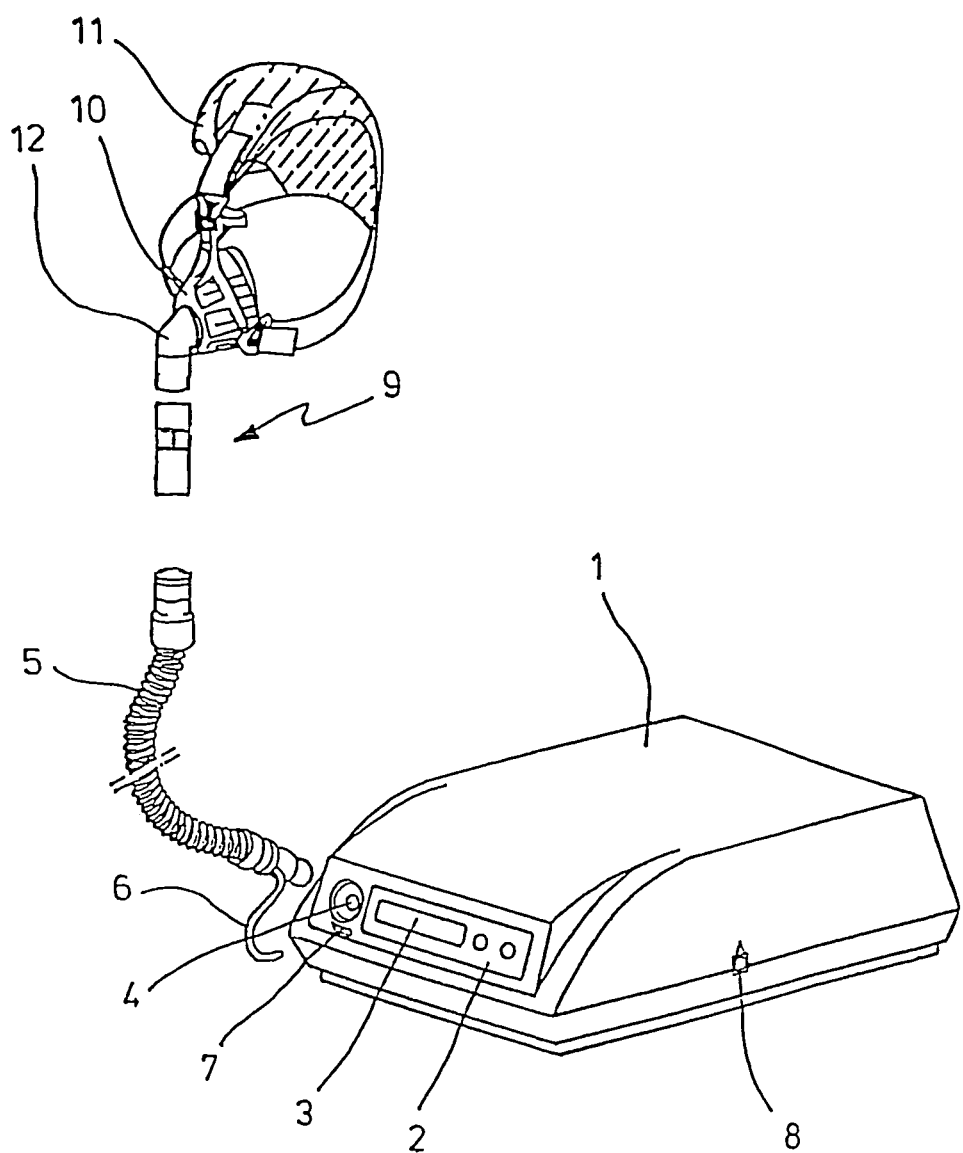
FIG. 1 is a perspective view of a ventilation device with a connecting hose running to a ventilation mask.

FIG. 1 shows the basic configuration of a ventilation device. In the area of the unit housing 1, which has an operating panel 2 and a display 3, a respiratory gas pump is installed in an internal space in the unit. A respiratory gas hose 5 is attached by a coupling 4. An additional pressure-measuring hose 6, which can be connected with the unit housing 1 by a pressure input connection 7, can run along the respiratory gas hose 5. To allow data transmission, the unit housing 1 has an interface 8.

An expiratory device 9 is installed in an expanded area of the respiratory gas hose 5 that faces away from the unit housing 1. An expiratory valve can also be used.

FIG. 1 also shows a ventilation mask 10, which is a nasal mask. The mask can be fastened on the head of a patient by a head fastening device 11. A hose coupling 12 is provided in the expanded region of the ventilation mask 10 that faces the respiratory gas hose 5.

Figure 2:
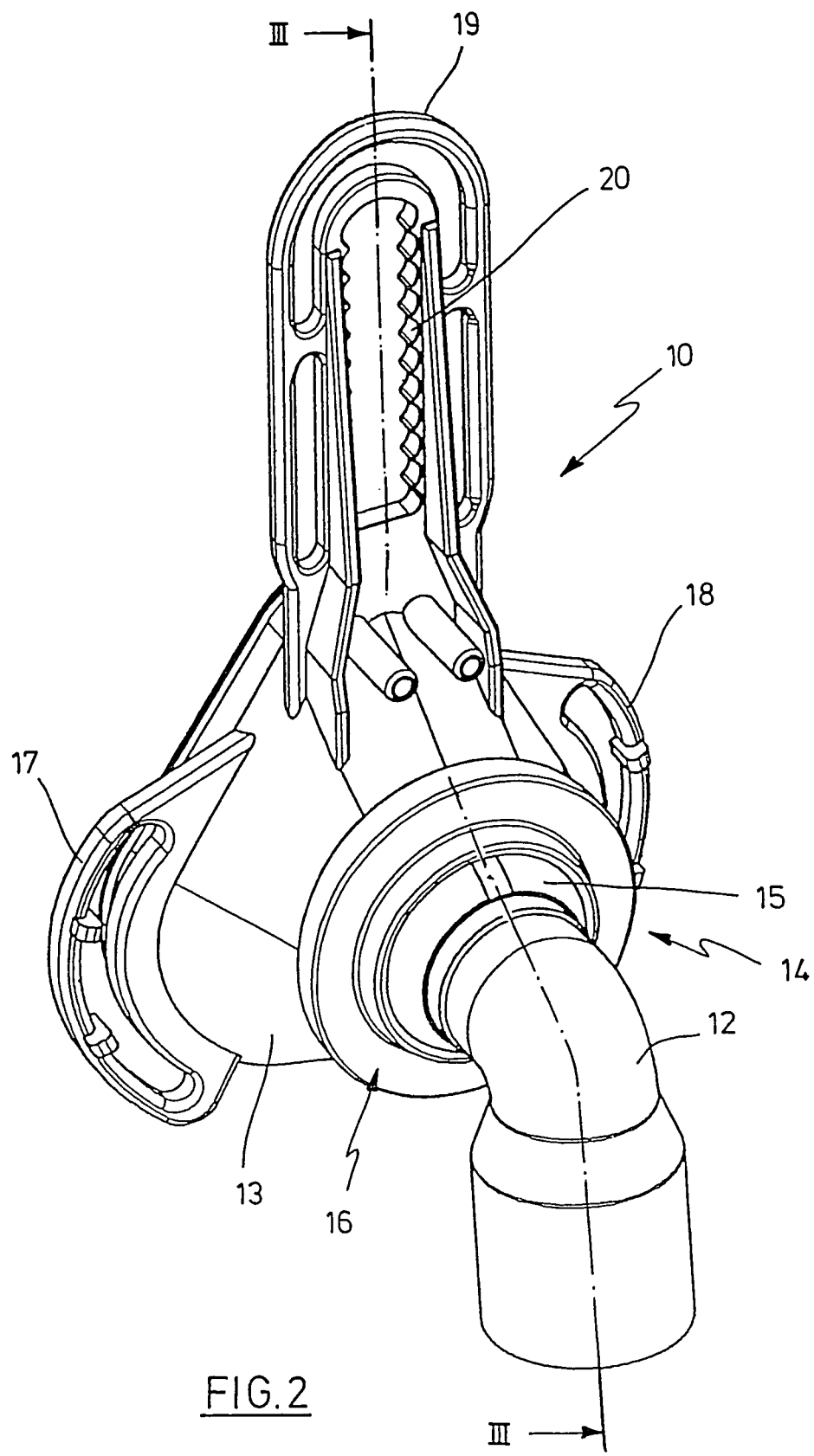
FIG. 2 is a perspective view of a ventilation mask with a ball-and-socket joint.

FIG. 2 shows the design of the ventilation mask 10 in detail. The hose coupling 12 for the respiratory gas hose 5, which is not shown in this drawing, is connected with the base 13 of the ventilation mask 10 by a joint 14, which is a ball-and-socket joint. In the embodiment illustrated here, the joint 14 consists of an inner part 15, which is joined with the hose coupling 12, and an outer shell 16, which is joined with the base 13 of the mask. The inner part 15 is designed at least regionally as a spherical segment, and the outer shell 16 extends along at least a portion of the surface of the inner part 15 that is shaped like a spherical segment. As it is evident from FIG. 2, the joint (14) has a contour due to the spherical configuration of the joint segments, which extends around the longitudinal axis as well as in the direction of the longitudinal axis in such a way that different portions of the joint parts are located at different distances from the longitudinal axis.

The base 13 of the mask has lateral fastening webs 17, 18 for attaching the head fastening device 11, which is not shown in FIG. 2, and a nosepiece 19, which is also used for attaching the head fastening device 11. The drawing also shows a catch 20 for positioning a forehead support not shown.

Figure 3:
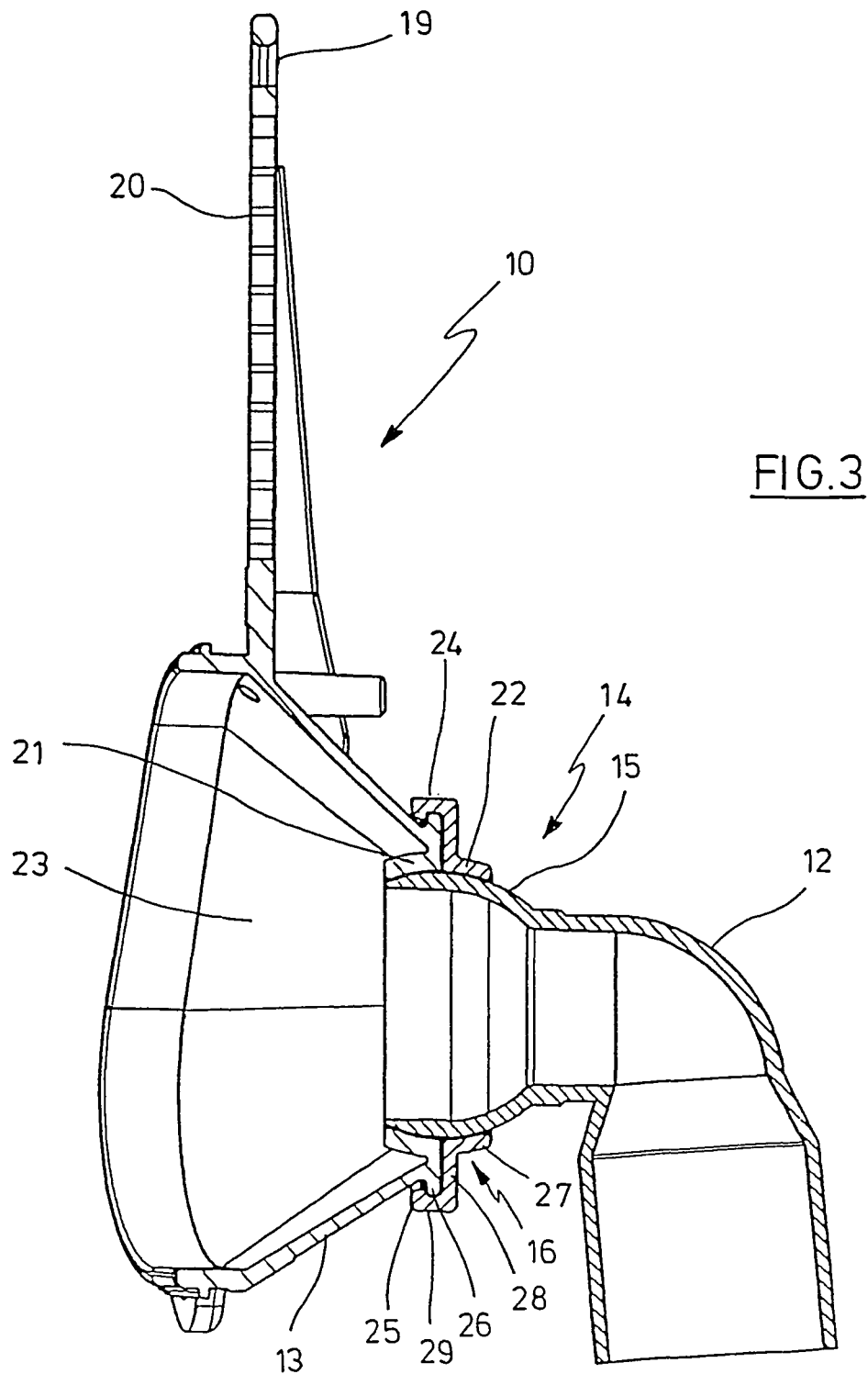
FIG. 3 is a vertical section along cross-sectional line III-III in FIG. 2.

The vertical section in FIG. 3 illustrates that the outer shell 16 comprises a first shell segment 21 and a second shell segment 22. The first shell segment 21 is formed on the base 13 and extends at least regionally into an interior space 23 of the mask. The second shell segment 22 is formed as part of a securing device 24, which in the illustrated embodiment is realized as a securing ring.

The securing device 24 has a locking profile 25 that engages a mating profile 26 of the base 13. In the embodiment illustrated in FIG. 3, the locking profile 25 is formed as a protruding edge, which grips behind the mating profile 26 in the manner of a snap connection. In the embodiment in FIG. 3, the securing device 24 consists essentially of a guide web 27, which rests against the inner part 15, a radial web 28, which runs essentially perpendicularly to the guide web 27, and a transverse web 29, which carries the locking profile 25. The guide web 27 is formed as a spherical surface of the shell half.

Figure 4:
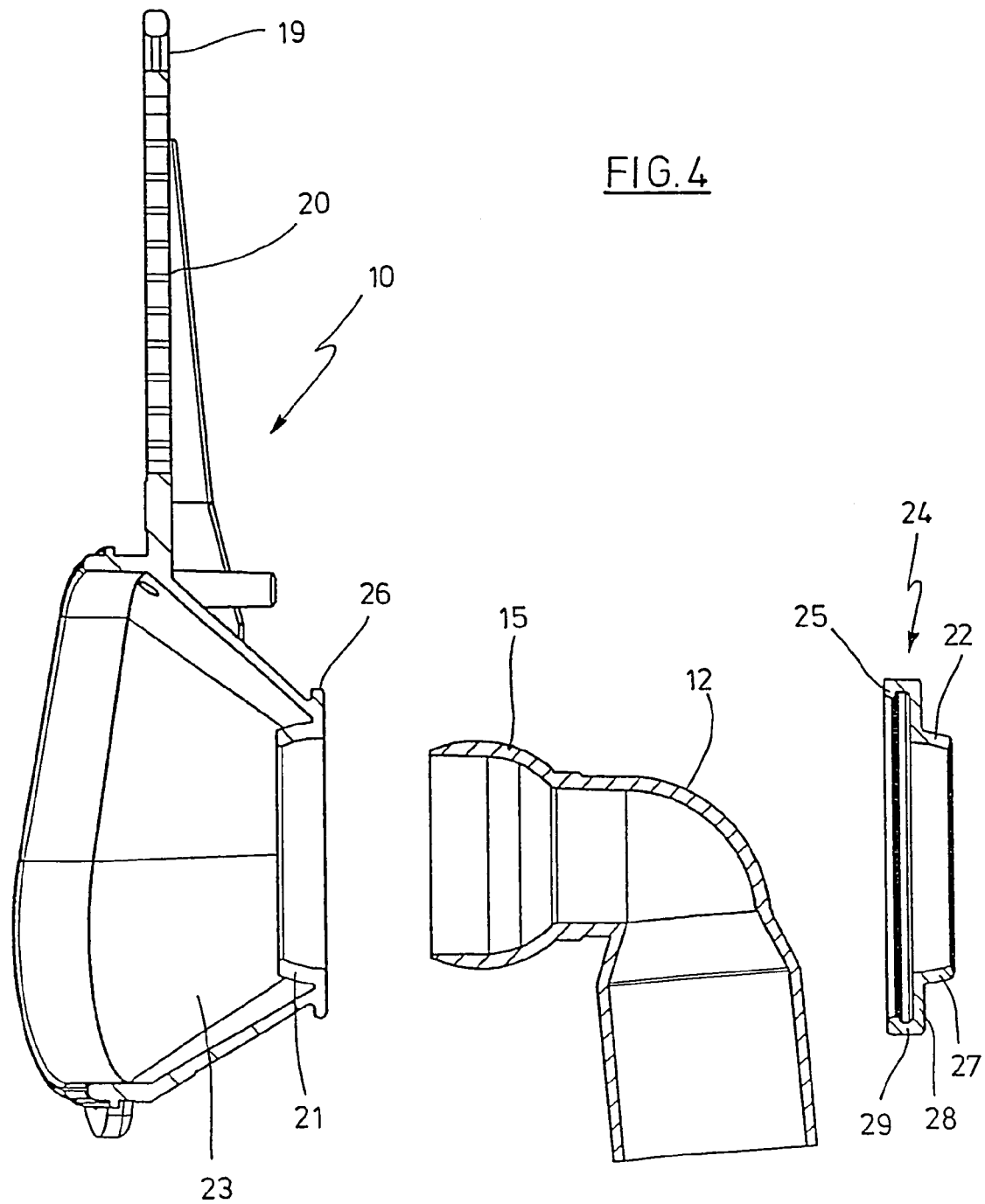
FIG. 4 is an exploded view of the components in FIG. 3.

The exploded view in FIG. 4 shows the geometry of the individual parts in FIG. 3. The parts can be assembled, for example, by first pushing the securing device 24 over the hose coupling 12 and then pushing the inner part 15 into the first shell segment 21. The locking profile 25 is then snapped into the mating profile 26, so that the securing device 24 is held on the base 13. In this assembled state, the inner part 15 is supported in such a way that it can both rotate and support the load of the shell segments 21, 22.

Figure 5:
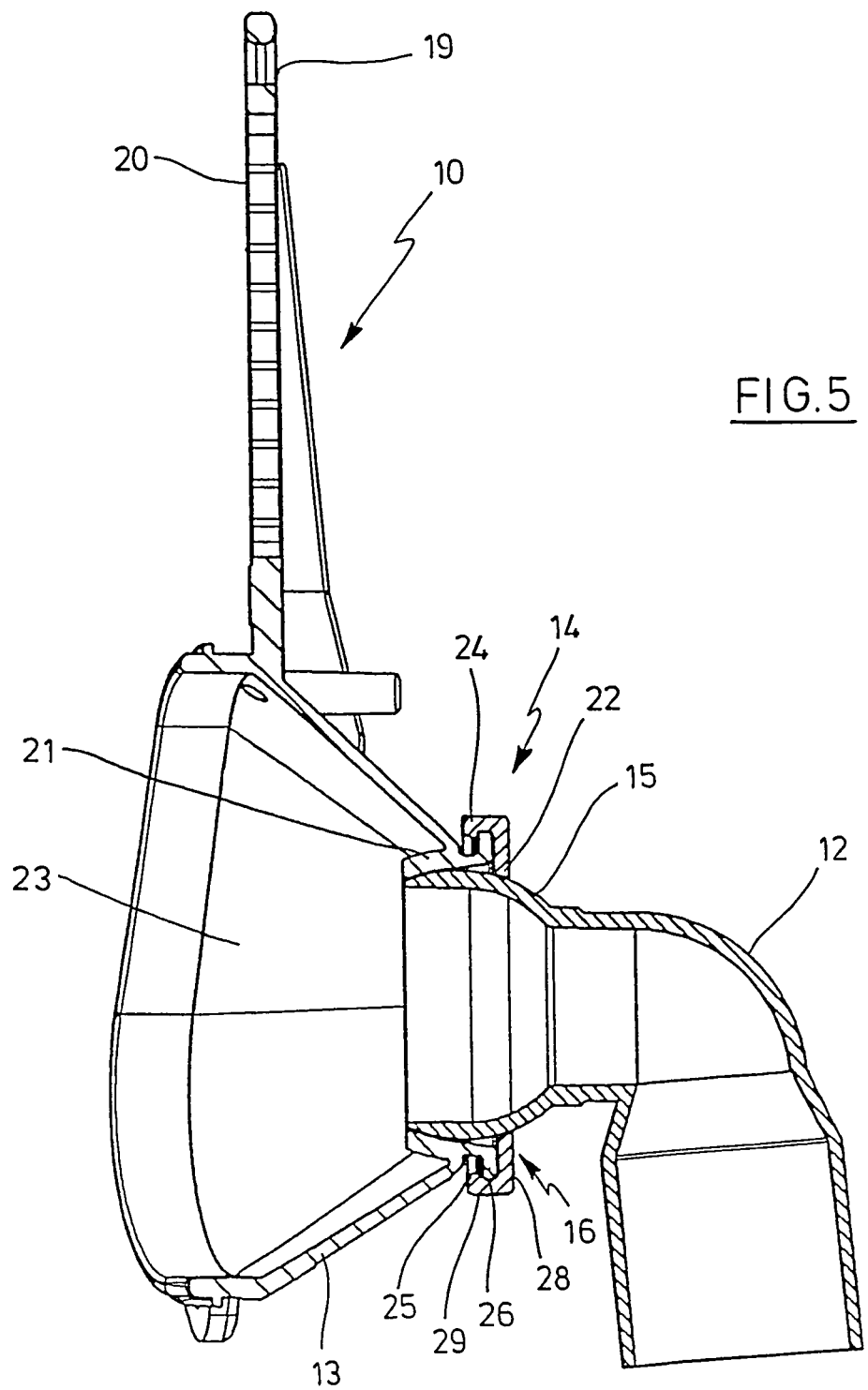
FIG. 5 shows a modification of the embodiment shown in FIG. 3 with a smaller guide surface in the area of the securing ring.

In the embodiment shown in FIG. 5, the securing device 24 is constructed without the guide web 27, and the second shell segment 22 is arranged in the area of the inner terminal end of the radial web 28 that faces the inner part 15. This geometric design helps simplify the production of the securing device 24. The second shell segment 22 provides a separate contact surface relative to the spherical surface, so that line contact is approximately realized between the two surfaces. The line contact can be realized in either of the two shell halves separately or in both shell halves.

Figure 6:
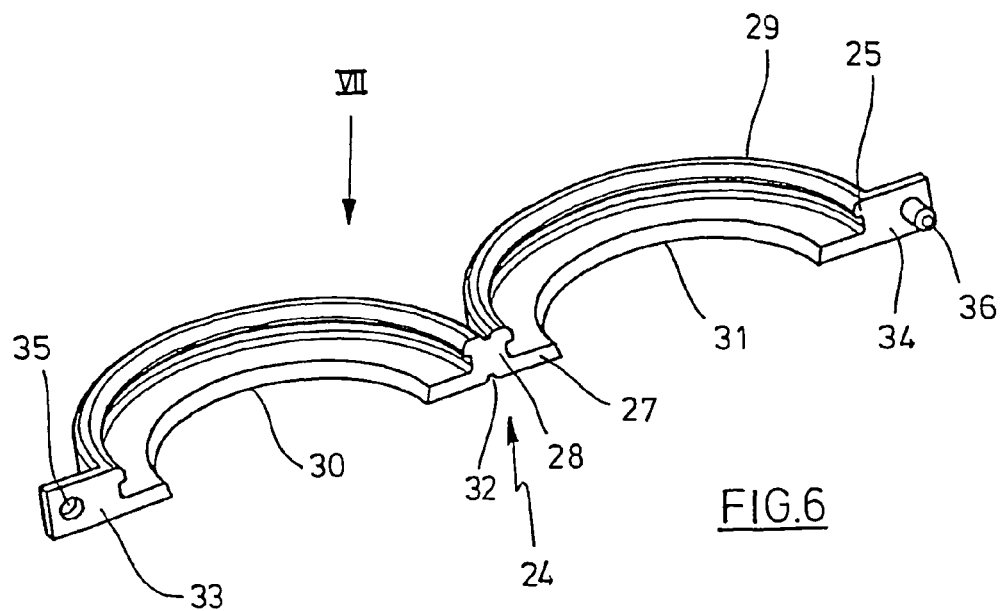
FIG. 6 is a perspective view of a single-part hinged securing ring.
Figure 7:
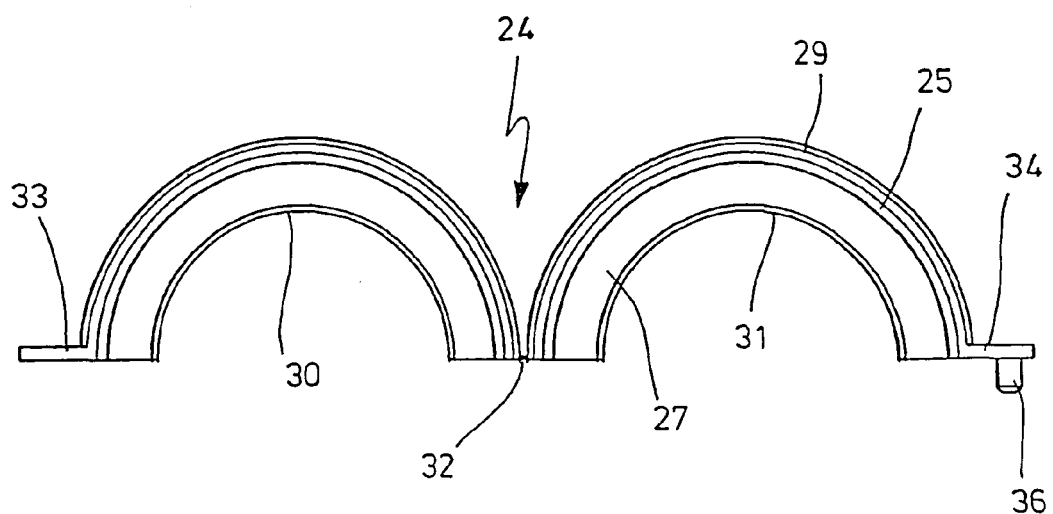
FIG. 7 is a top view of the securing ring in viewing direction VII in FIG. 6.

In the drawings in FIGS. 6 and 7, the securing device 24 is a hinged ring. The securing device 24 consists of two half rings 30, 31 joined by a film hinge 32. In the area of their terminal ends that face away from the film hinge 32, the half rings 30, 31 have joint webs 33, 34. One of the joint webs 33 has a recess 35, and the other joint web 34 has a pin 36, so that when the terminal ends of the half rings 30, 31 are brought together, the pin 36 snaps into the recess 35, and a closed ring is formed. The constructional realization of the securing device 24 is illustrated in a perspective view in FIG. 6 and in a top view in FIG. 7.

Figure 8:
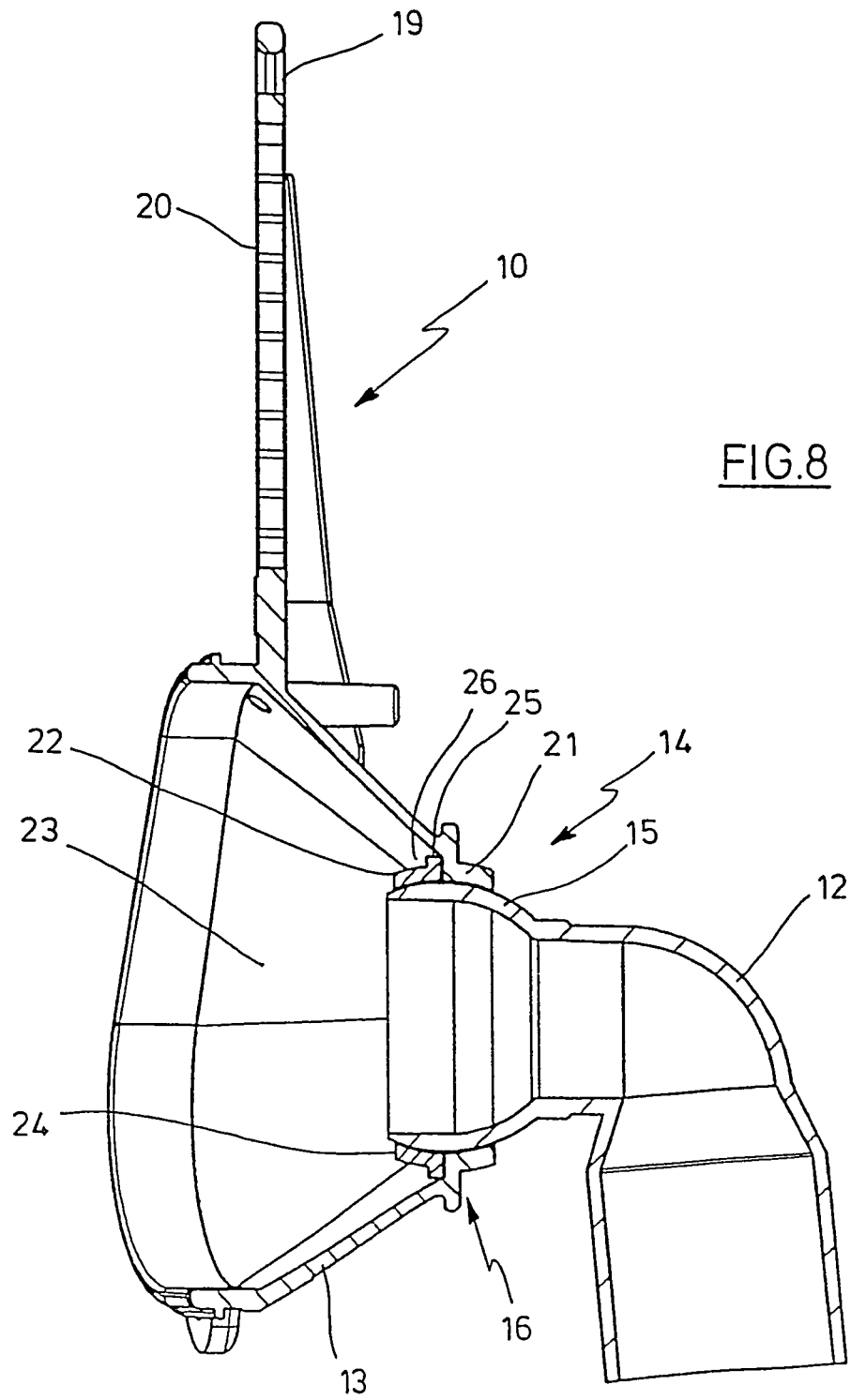
FIG. 8 shows another modification of the embodiment shown in FIG. 3, in which the securing ring is arranged on the inside in the area of the ventilation mask.

In the embodiment illustrated in FIG. 8, the securing device 24 with the second shell segment 22 is arranged on the inside with respect to the interior 23 of the mask, and the shell segment 21 that is formed as part of the base 13 is positioned in the expanded area of the joint 14 that faces the hose coupling 13. In this embodiment as well, the securing device 24 can also extend essentially annularly and has a locking profile 25 that engages a mating profile 26 of the base 13.

Figure 9:
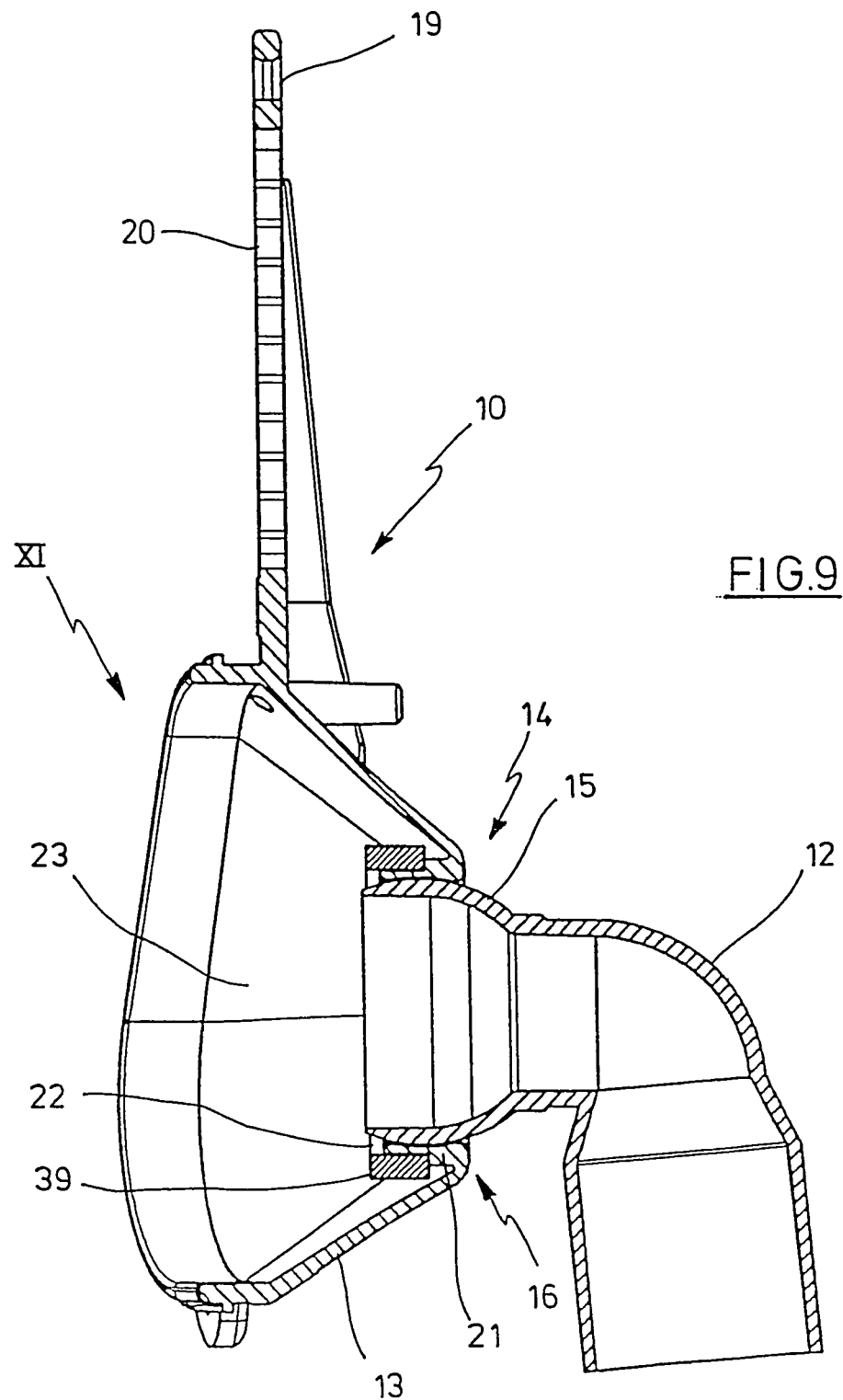
FIG. 9 shows a modification of the embodiment shown in FIG. 8, in which teeth are provided as a catch mechanism.

The embodiment shown in FIG. 9 has a fundamentally different design from the embodiments previously discussed. In this embodiment, the main part of the outer shell 16 is formed by the first shell segment 21, which is formed on the base 13. The first shell segment 21 provides a single-part seat for the inner part 15 and is elastically deformable in its installed state. After a securing ring 39 has been mounted, functional elastic deformability no longer exists. The securing ring 39 provides only a relatively small second shell segment 22, which essentially prevents the inner part 15 from being pushed into the interior 23 of the mask by mechanical stabilization of the bearing seat and does not itself support the inner part 15.

Figure 10:
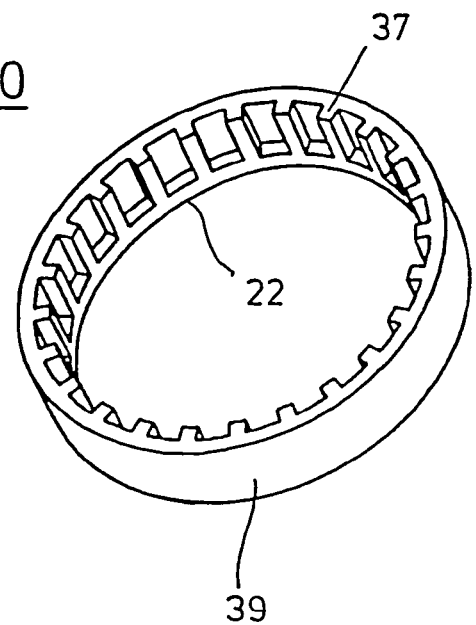
FIG. 10 is a perspective view of the securing ring in FIG. 9.

The securing ring 39 shown in FIG. 9 is further illustrated in FIG. 10, which shows that the securing ring 39 is essentially circular and has internal teeth 37 that extend into the area of the second shell segment 22. The securing ring does not touch the inner part 15.

Figure 11:
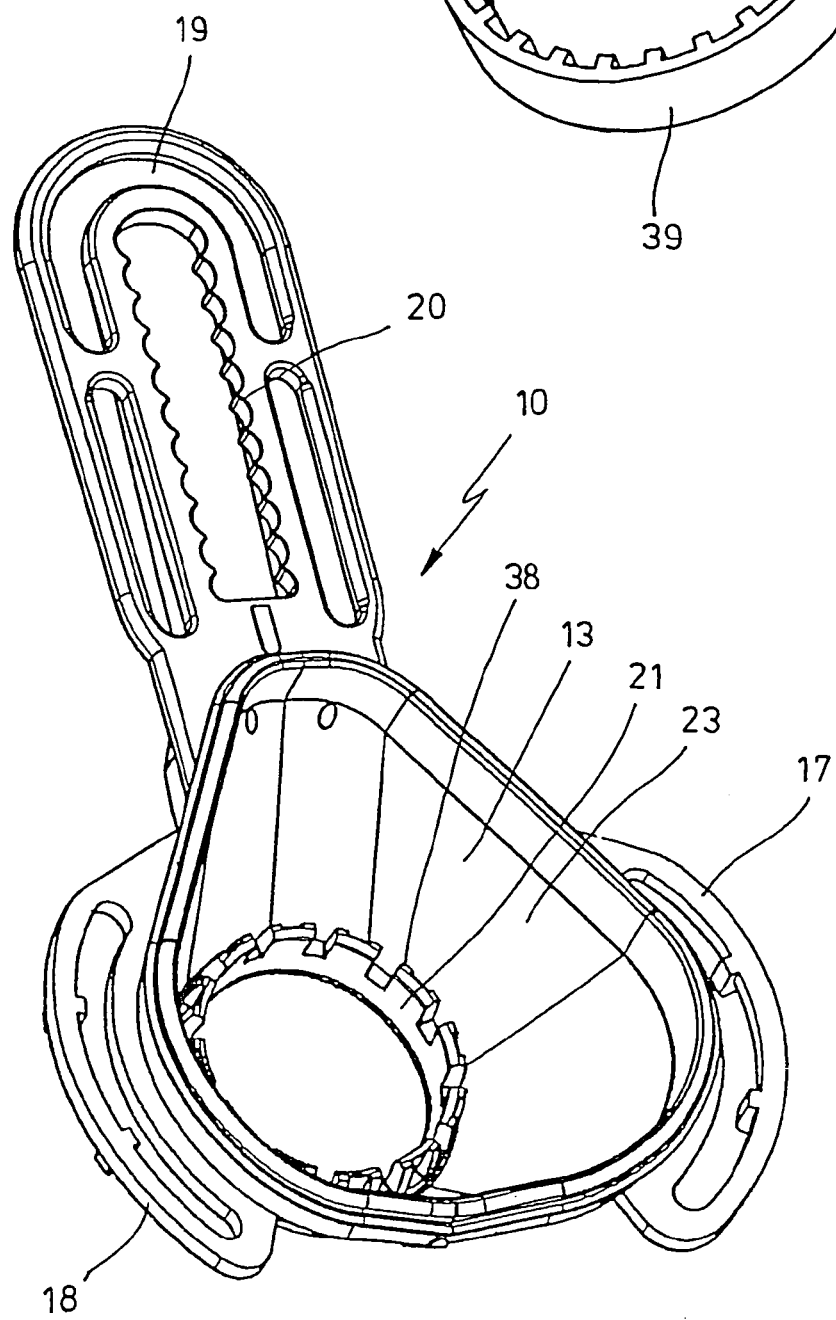
FIG. 11 is a perspective view in viewing direction XI in FIG. 9 with the securing ring detached.

The perspective drawing in FIG. 11 shows that the first shell segment 21 is also provided with teeth 38, which can be pushed apart towards the outside when the inner part 15 is inserted. After the inner part 15 has been positioned, and the securing ring 39 has been pushed on, the teeth 38 of the first shell segment 21 are protected from outward bending, so that reliable mounting of the inner part 15 is achieved, and at the same time sufficient mobility is ensured.

An essential advantage of the use of a single-part first shell segment 21 is that it provides a guide surface that is seamless and without discontinuities, so that the ball-and-socket joint runs extremely smoothly. As a result of the fact that the guide elements are elastically deformable in the installed state, when the securing ring 39 is not mounted, assembly and disassembly of the inner part 15 can be accomplished without applying much force and without causing mechanical damage to the components that are used. Only after the securing ring 39 has been mounted, is an essentially rigid total structure obtained, which prevents the inner part 15 both from being pulled out of the joint guide and from being pushed into the interior 13 of the mask.

We claim:

1. A ventilation device, comprising a ventilation mask configured to be connected to a respiratory gas hose and having a respiratory gas hose coupling movably connected by a joint with a base of the ventilation mask, wherein the joint is comprised of a ball-and-socket joint, the joint having an inner part shaped as a spherical segment and an outer shell for guiding the inner part, and wherein the outer shell is constructed from at least two shell segments that can be connected with each other, wherein the first shell segment is formed on the base of the mask, wherein the second shell segment is a ring installed near a securing device, wherein the outer shell is formed at least over portions thereof in the form of spherical segments, wherein the spherical segments extend spherically in a direction of a longitudinal axis of the joint, wherein the joint has a joint contour due to the spherical configuration of the joint segments which extends around the longitudinal axis as well as in the direction of the longitudinal axis in such a way that different portions of the joint parts are located at different distances from the longitudinal axis, and wherein there is line contact between the first shell segment and the inner part, wherein the securing device is clamped to the first shell segment.

2. The device in accordance with claim 1, wherein the inner part is formed as part of the hose coupling.

3. The device in accordance with claim 1, wherein the shell segments are coupled by at least one snap connection.

4. The device in accordance with claim 1, wherein the second shell segment has a guide web for applying force on the inner part.

5. The device in accordance with claim 1, wherein the securing device is locked with the first shell segment by a catch.

6. The device in accordance with claim 1, wherein the securing device is screwed together with the first shell segment.

7. The device in accordance with claim 1, wherein the securing device is a closed ring.

8. The device in accordance with claim 1, wherein the securing device is a hinged ring.

9. The device in accordance with claim 1, wherein the securing device is provided with internal teeth.

10. The device in accordance with claim 1, wherein the joint is arranged outside of the ventilation mask between the base of the mask and the respiratory gas hose.

11. The device in accordance with claim 1, wherein the securing device is arranged outside with respect to an interior of the mask.

12. The device in accordance with claim 1, wherein the securing device is arranged inside with respect to an interior of the mask.

13. The device in accordance with claim 1, wherein the securing device encloses at least portions of teeth of the first shell segment.

14. Device in accordance with claim 1, wherein both shell segments are configured to guide the inner part.

15. Device in accordance with claim 1, wherein only the first shell segment is configured to guide the inner part, and that the second shell segment is configured for mechanical stabilization of the first shell segment.

* * * * *